United States Patent
Kurtz et al.

(10) Patent No.: US 10,077,724 B1
(45) Date of Patent: Sep. 18, 2018

(54) METHODS AND SYSTEMS FOR A FUEL INJECTOR

(71) Applicant: Ford Global Technologies, LLC, Dearborn, MI (US)

(72) Inventors: Eric Matthew Kurtz, Dearborn, MI (US); Christopher Polonowski, Belleville, MI (US); Daniel William Kantrow, Ann Arbor, MI (US); Daniel Joseph Styles, Canton, MI (US); Paul Joseph Tennison, West Bloomfield, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 2 days.

(21) Appl. No.: 15/461,238

(22) Filed: Mar. 16, 2017

(51) Int. Cl.
| | | |
|---|---|---|
| F02D 35/02 | (2006.01) | |
| F02D 41/00 | (2006.01) | |
| F02D 41/26 | (2006.01) | |
| F02D 19/12 | (2006.01) | |
| F02F 1/24 | (2006.01) | |
| G01N 21/61 | (2006.01) | |

(52) U.S. Cl.
CPC .......... *F02D 35/025* (2013.01); *F02D 19/12* (2013.01); *F02D 41/0002* (2013.01); *F02D 41/0052* (2013.01); *F02D 41/26* (2013.01); *F02F 1/242* (2013.01); *G01N 21/61* (2013.01)

(58) Field of Classification Search
CPC ........ F02D 35/02; F02D 35/025; F02D 41/00; F02D 41/0002; F02D 41/0052; F02D 41/26; F02D 19/12; F02F 1/142; G01N 21/61
See application file for complete search history.

(56) References Cited

U.S. PATENT DOCUMENTS

| | | | |
|---|---|---|---|
| 4,327,547 A | 5/1982 | Hughes et al. | |
| 4,513,937 A * | 4/1985 | Langmesser, Jr. ... | B60N 2/1803 248/394 |
| 9,285,114 B2 * | 3/2016 | Tsumagari ............ | F23D 11/408 |
| 9,587,606 B2 | 3/2017 | Anders et al. | |
| 2016/0097360 A1 | 4/2016 | Mueller | |
| 2017/0114763 A1 | 4/2017 | Mueller | |
| 2017/0114998 A1 | 4/2017 | Mueller | |

FOREIGN PATENT DOCUMENTS

WO   2015153115 A1   10/2015

OTHER PUBLICATIONS

Polonowski, C. et al., "Controlled Air Entertainment Passage for Diesel Engines," U.S. Appl. No. 15/170,561, filed Jun. 1, 2016, 75 pages.

* cited by examiner

*Primary Examiner* — Hieu T Vo
(74) *Attorney, Agent, or Firm* — Julia Voutyras; McCoy Russell LLP

(57) ABSTRACT

Methods and systems are provided for a fuel injector coupled to mixing passages for entraining combustion chamber gases with a fuel injection to decrease formation of soot throughout a range of engine operating parameters. In one example, a method includes decreasing a combustion chamber temperature in response to an amount of sensed light.

20 Claims, 7 Drawing Sheets

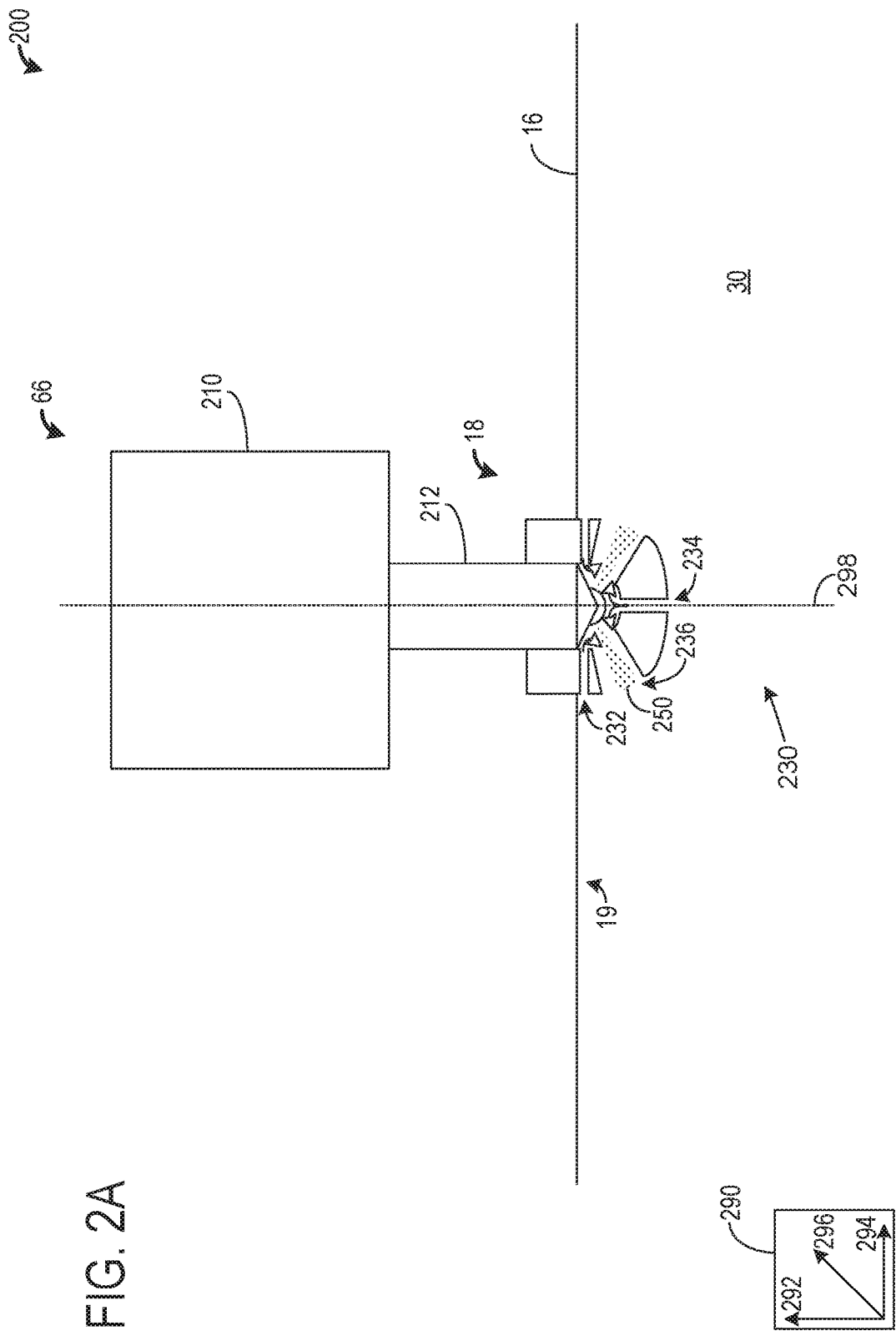

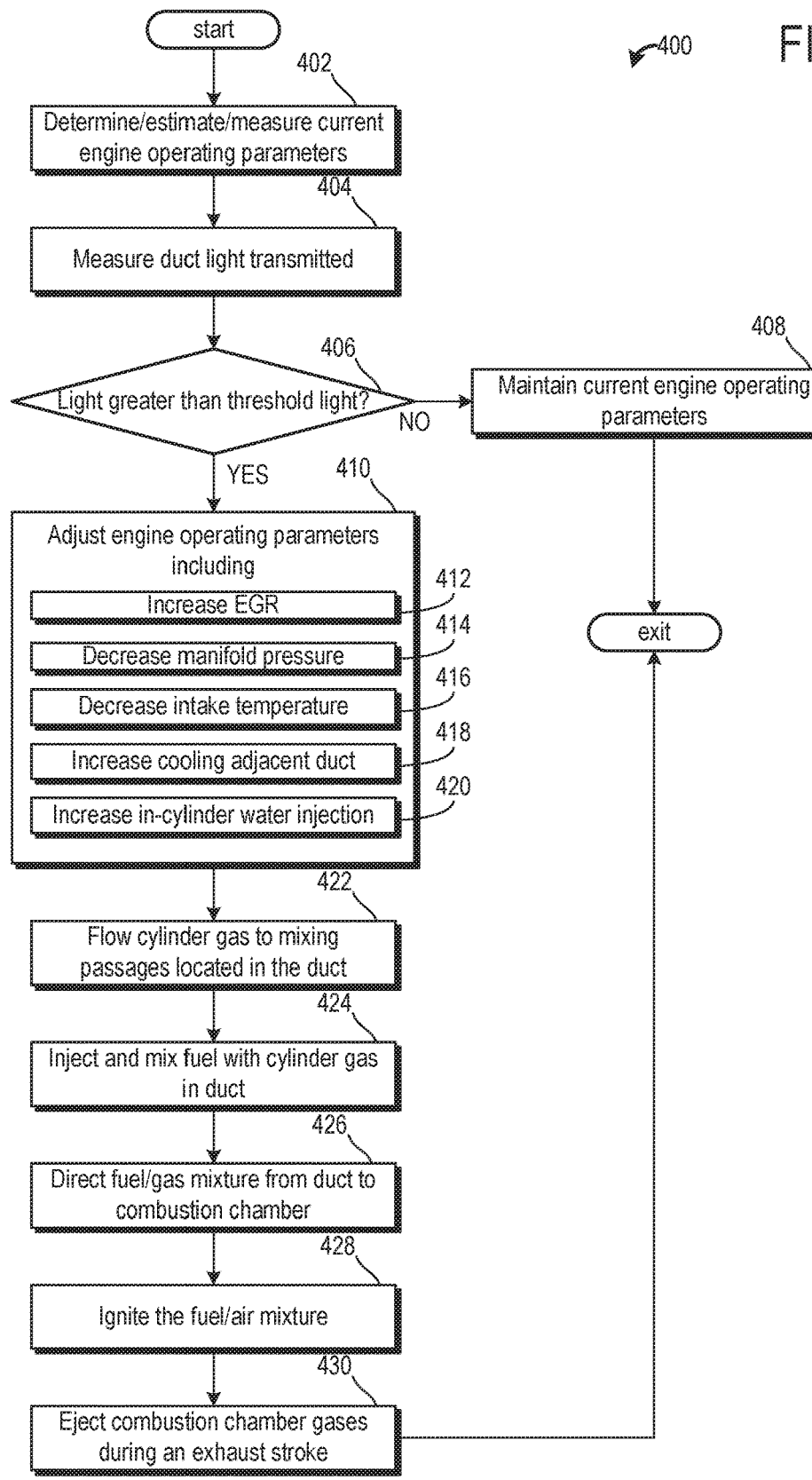

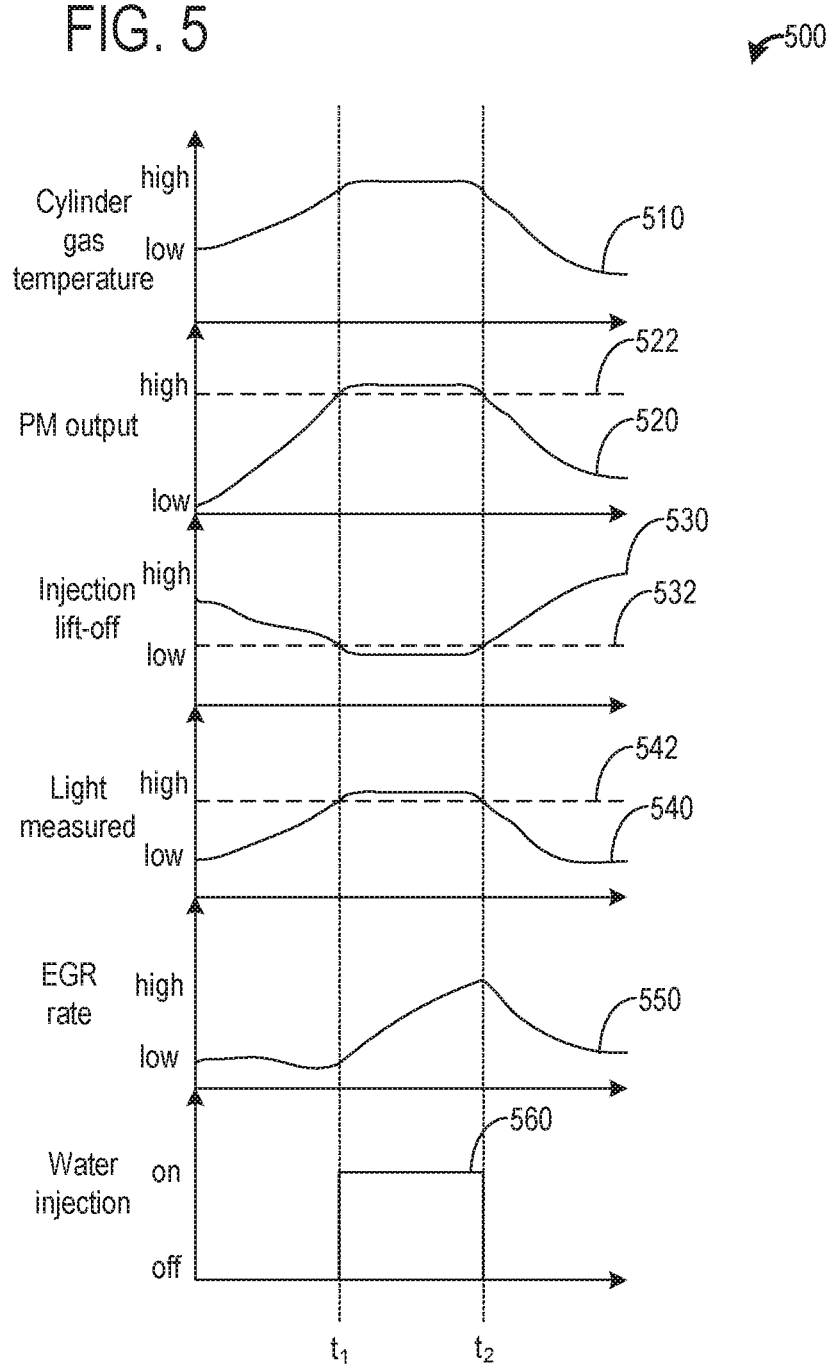

METHODS AND SYSTEMS FOR A FUEL INJECTOR

FIELD

The present description relates generally to methods and systems for a fuel injector comprising air entrainment features.

BACKGROUND/SUMMARY

In diesel engines, air is drawn into a combustion chamber during an intake stroke by opening one or more intake valves. Then, during the subsequent compression stroke, the intake valves are closed, and a reciprocating piston of the combustion chamber compresses the gases admitted during the intake stroke, increasing the temperature of the gases in the combustion chamber. Fuel is then injected into the hot, compressed gas mixture in the combustion chamber, resulting in combustion of the fuel. Thus, in a diesel engine, the fuel may combust with the air in the combustion chamber due to the high temperature of the air, and may not be ignited via a spark plug as in a gasoline engine. The combusting air-fuel mixture pushes on the piston, driving motion of the piston, which is then converted into rotational energy of a crankshaft.

However, the inventors have recognized potential issues with such diesel engines. As one example, diesel fuel may not mix evenly with the air in the combustion chamber, leading to the formation of dense fuel pockets in the combustion chamber. These dense regions of fuel may produce soot as the fuel combusts. As such, conventional diesel engines include particulate filters for decreasing an amount of soot and other particulate matter in their emissions. However, such particulate filters lead to increased cost and increased fuel consumption.

Modern technologies for combating engine soot output include features for entraining air with the fuel prior to injection. This may include passages located in the injector body, as an insert into the engine head deck surface, or in engine head. Ambient air mixes with the fuel, cooling the injection temperature, prior to delivering the mixture to the compressed air in the cylinder. By entraining cooled air with the fuel prior to injection, a lift-off length is lengthened and start of combustion is retarded. This limits soot production through a range of engine operating conditions, reducing the need for a particulate filter.

However, the inventors herein have recognized potential issues with such injectors. As one example, the previously described fuel injectors may no longer sufficiently prevent soot production to a desired level in light of increasingly stringent emissions standards. As such, particulate filters may be located in an exhaust passage, thereby increasing a manufacturing cost and packaging restraint of the vehicle.

In one example, the issues described above may be addressed by a system comprising a fuel injector comprising a nozzle tip submerged into a combustion chamber below a cylinder head, the nozzle tip comprising one or more fuel injection orifices configured to inject at an angle relative to a central axis of the fuel injector and one or more mixing passages configured to receive a fuel injection or combustion chamber gases, where the one or more mixing passages configured to receive the fuel injection are oblique to the central axis and are aligned with the fuel injection orifices, and where the one or more mixing passages configured to receive combustion chamber gases include passage perpendicular to and parallel to the central axis, where the one or more mixing passage configured to receive the fuel injection are configured to receive combustion chamber gases from the one or more mixing passages configured to receive combustion chamber gases via one or more of a venturi passage and a louver. In this way, soot production is limited or prevented when pre-combustion is detected in the passage.

As one example, the mixing passages are integrated into one or more of a duct and nozzle tip of the fuel injector. First and second mixing passages of the mixing passages are configured to receive combustion chamber gases during a compression stroke of the cylinder. A third mixing passage receive the fuel injection and is configured to receive the combustion chamber gases from the first and second mixing passages via the venturi passage and/or louver. By mixing the fuel and air prior to releasing the fuel to the combustion chamber, the dense pockets of fuel described above may be avoided. A light sensor in the third mixing passage may determine if the mixture has combusted prior to flowing out of the passage to the engine. If this has occurred, then one or more engine operating parameters are adjusted to decrease a combustion chamber temperature. By doing this, a compact, and easy to manufacture duct and/or nozzle tip may decrease and/or prevent soot production during a wide range of engine operating conditions.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIG. 2A shows a side, cross-sectional view of an injector and a duct of the fuel-air mixing chamber.

FIGS. 2A-3 are shown approximately to scale.

FIG. 4 shows a method for adjusting in cylinder operating conditions in response to an emissions output.

FIG. 5 shows an operational sequence based on the engine system of FIG. 1 implementing the method illustrated in FIG. 4.

DETAILED DESCRIPTION

The following description relates to systems and methods for injecting fuel into an engine cylinder. In particular, the following description relates to systems and methods for injecting diesel fuel. An engine system, such as the engine system shown in FIG. 1, may comprise one or more engine cylinders, each comprising at least one fuel injector. The fuel injectors may be direct injectors that inject fuel directly into the engine cylinders. However, when injected directly into the cylinders, diesel fuel may not mix evenly with the air in the cylinders, leading to pockets in the cylinders of denser and/or less oxygenated fuel where soot may be produced during the combustion cycle.

To reduce the amount of soot produced by an engine, air passages may be included in the engine. Specifically, the air passages may be positioned in a portion of a nozzle of the fuel injector in fluidic communication with and located within the combustion chambers. In this way, gases from a combustion chamber may flow through the air passages, where the gases may mix with a fuel injection prior to combustion. This may improve air-fuel mixing and decrease a likelihood of fuel pocket formation.

To further reduce the amount of soot produced by the engine, one or more ducts may be associated with each fuel injector of the engine. The ducts may comprise one or more air entrainment features configured to mix cylinder air with the fuel injection prior to injecting. In one example, the air entrainment features correspond to outlets of the cooled-air passages. This may prevent pre-ignition of the fuel injection while extending a lift-off length and retarding start of ignition. As such, homogeneity of the air-fuel mixture is increased, mitigating formation of fuel pockets in the cylinder.

In some examples, such as described in FIGS. 2A-2C, the air passages may be included in a duct coupled to the fuel injector and protruding into a cylinder space below a cylinder head. The duct is configured to increase air-fuel mixing via surface features located therein.

In other examples, such as those shown in FIG. 3, the air passages may be machined into a portion of the fuel injector protruding into the cylinder space below a cylinder head. The air passages may increase air-fuel mixing via an interfacing between the air passages and fuel passages.

In some examples, methods and systems include adjusting engine operating parameters based on in-cylinder and/or in-nozzle or in-duct conditions. For example, a photodiode may monitor light emitted in the duct and/or nozzle, thereby indicating a combustion in the duct and/or nozzle. A method for adjusting the engine operating parameters based on light emitted is shown in FIG. 4. An example timeline for adjusting engine operating parameters based on the method of FIG. 4 is shown in FIG. 5.

Figure 1:
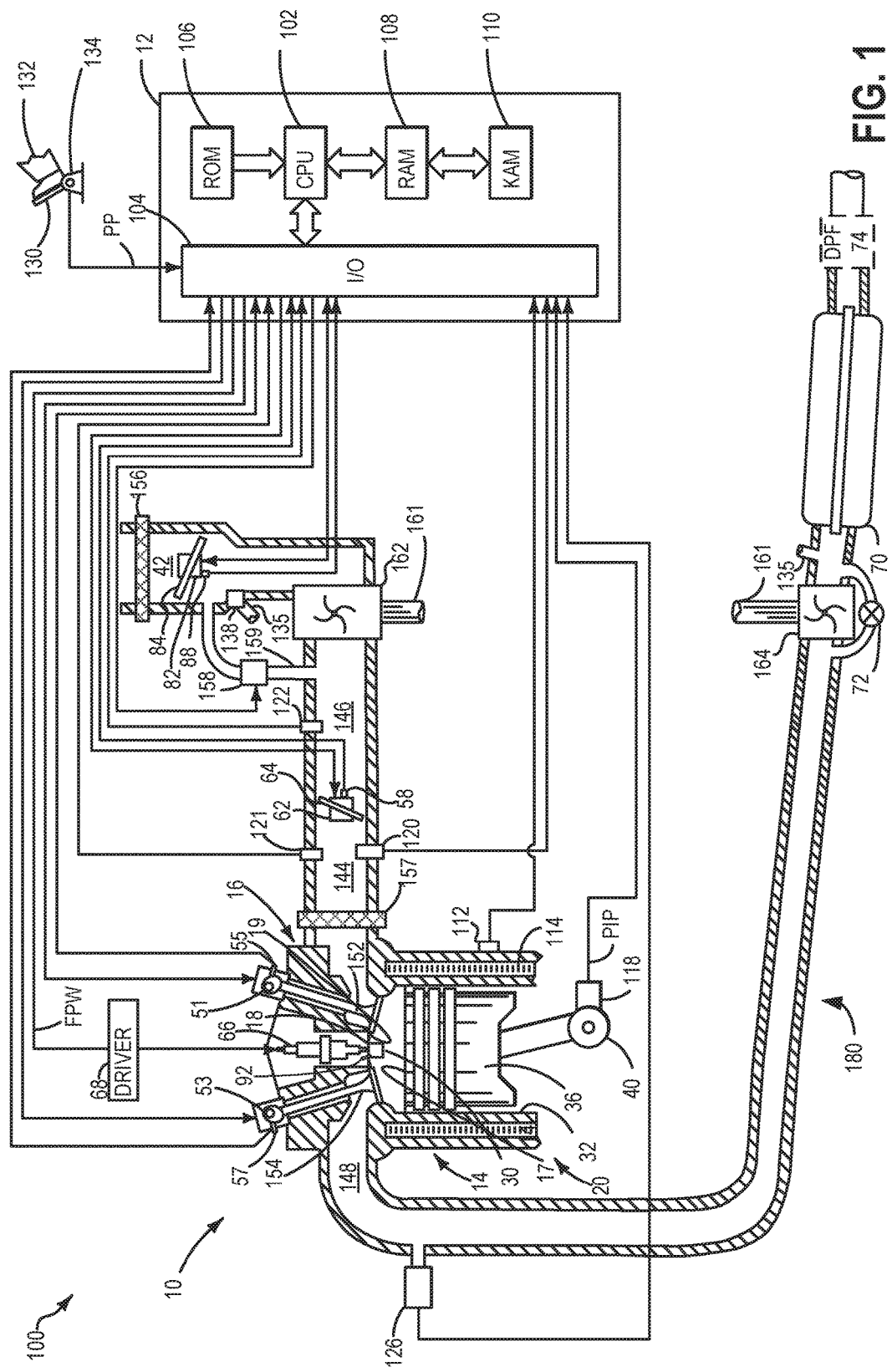
FIG. 1 shows a schematic diagram of an example engine system including a fuel-air mixing chamber.
Figure 2B:
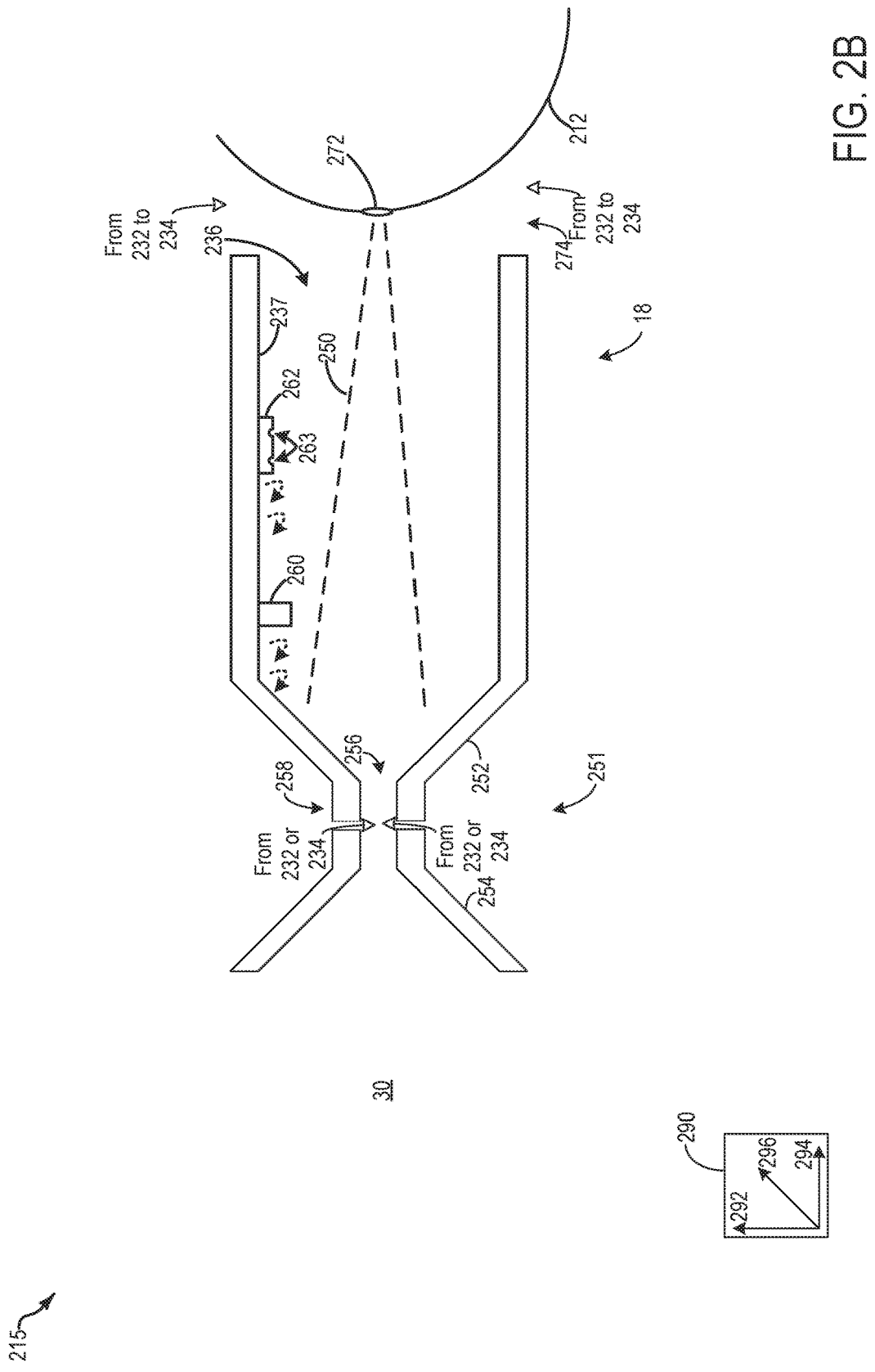
FIG. 2B shows a first embodiment of the duct.
Figure 2C:
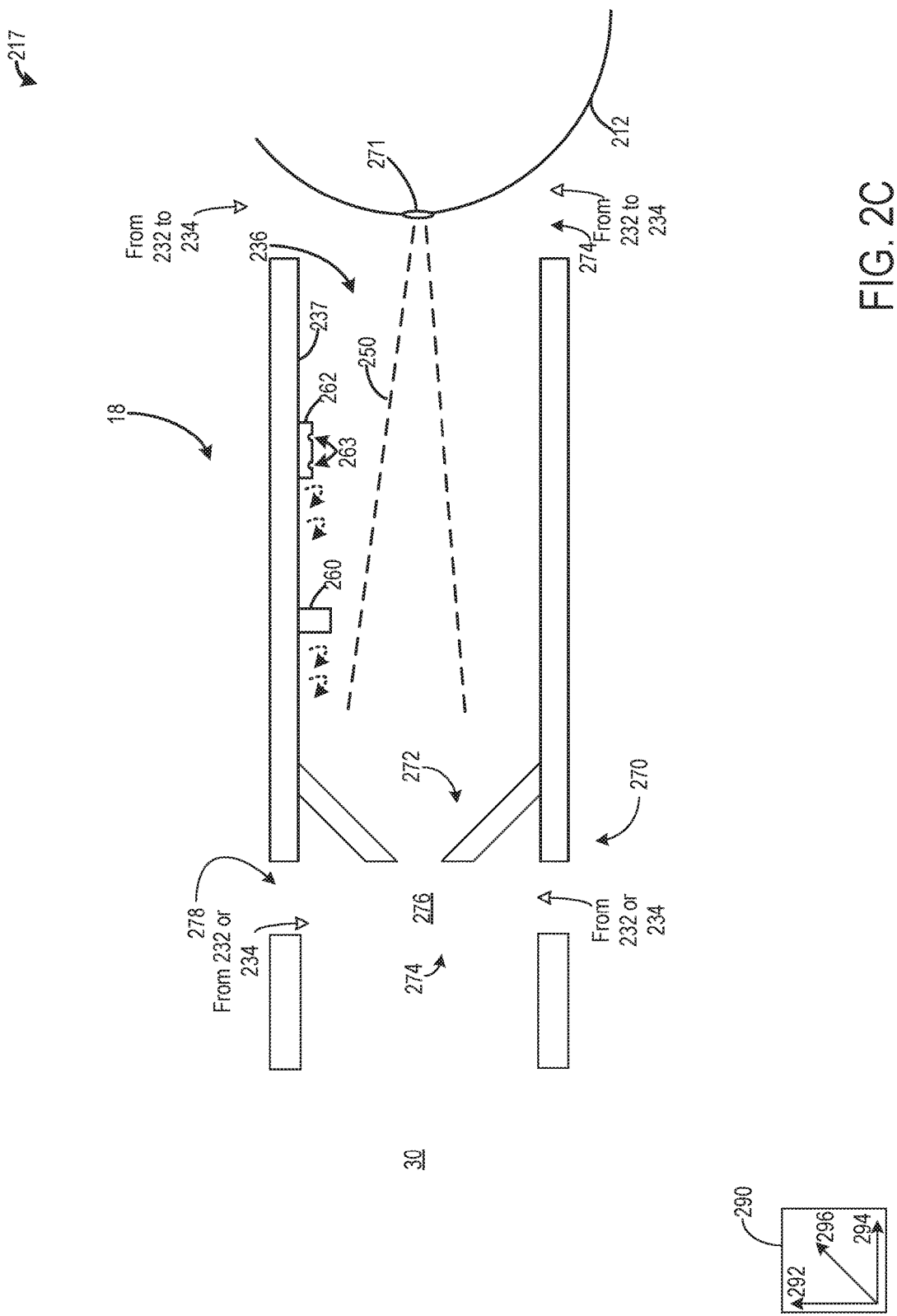
FIG. 2C shows a second embodiment of the duct.
Figure 3:
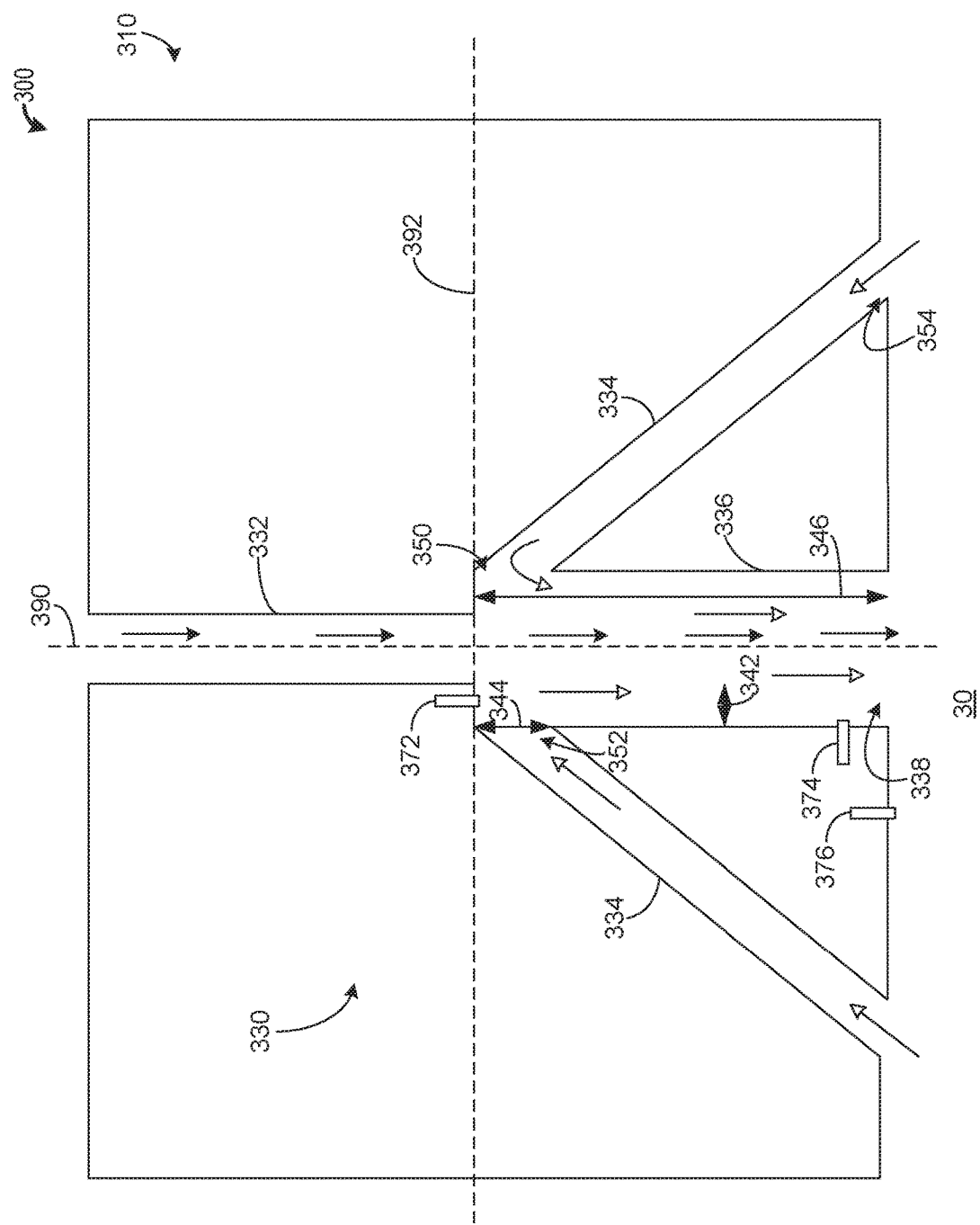
FIG. 3 shows an embodiment of an injector having an injector tip with mixing passages integrated therein.

FIGS. 1-3 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example. It will be appreciated that one or more components referred to as being "substantially similar and/or identical" differ from one another according to manufacturing tolerances (e.g., within 1-5% deviation).

Air in the combustion chambers may pass through the air passages and a more thorough and even mixing of the fuel and air may be achieved prior to combustion. In particular, the lift-off length, a term commonly used by those skilled in the art to describe the distance between the fuel spray and the combustion flame, may be increased. As such, more air may be entrained by the fuel prior to combustion. Thus, combustion may be delayed and air entrainment of the fuel may be increased, leading to a more complete and soot-free combustion.

FIG. 1 depicts an engine system 100 for a vehicle. The vehicle may be an on-road vehicle having drive wheels which contact a road surface. Engine system 100 includes engine 10 which comprises a plurality of cylinders. FIG. 1 describes one such cylinder or combustion chamber in detail. The various components of engine 10 may be controlled by electronic engine controller 12.

Engine 10 includes a cylinder block 14 including at least one cylinder bore 20, and a cylinder head 16 including intake valves 152 and exhaust valves 154. In other examples, the cylinder head 16 may include one or more intake ports and/or exhaust ports in examples where the engine 10 is configured as a two-stroke engine. The cylinder block 14 includes cylinder walls 32 with piston 36 positioned therein and connected to crankshaft 40. The cylinder bore 20 may be defined as the volume enclosed by the cylinder walls 32. The cylinder head 16 may be coupled to the cylinder block 14, to enclose the cylinder bore 20. Thus, when coupled together, the cylinder head 16 and cylinder block 14 may form one or more combustion chambers. In particular, combustion chamber 30 may be the volume included between a top surface 17 of the piston 36 and a fire deck 19 of the cylinder head 16. As such, the combustion chamber 30 volume is adjusted based on an oscillation of the piston 36. Combustion chamber 30 may also be referred to herein as cylinder 30. The combustion chamber 30 is shown communicating with intake manifold 144 and exhaust manifold 148 via respective intake valves 152 and exhaust valves 154. Each intake and exhaust valve may be operated by an intake cam 51 and an exhaust cam 53. Alternatively, one or more of the intake and exhaust valves may be operated by an electromechanically controlled valve coil and armature assembly. The position of intake cam 51 may be determined by intake cam sensor 55. The position of exhaust cam 53 may be determined by exhaust cam sensor 57. Thus, when the valves 152 and 154 are closed, the combustion chamber 30 and cylinder bore 20 may be fluidly sealed, such that gases may not enter or leave the combustion chamber 30.

Combustion chamber 30 may be formed by the cylinder walls 32 of cylinder block 14, piston 36, and cylinder head 16. Cylinder block 14 may include the cylinder walls 32, piston 36, crankshaft 40, etc. Cylinder head 16 may include one or more fuel injectors such as fuel injector 66, one or more intake valves 152, and one or more exhaust valves 154. The cylinder head 16 may be coupled to the cylinder block 14 via fasteners, such as bolts and/or screws. In particular, when coupled, the cylinder block 14 and cylinder head 16 may be in sealing contact with one another via a gasket, and as such may the cylinder block 14 and cylinder head 16 may seal the combustion chamber 30, such that gases may only flow into and/or out of the combustion chamber 30 via intake manifold 144 when intake valves 152 are opened, and/or via exhaust manifold 148 when exhaust valves 154 are opened. In some examples, only one intake valve and one exhaust valve may be included for each combustion chamber 30. However, in other examples, more than one intake valve and/or more than one exhaust valve may be included in each combustion chamber 30 of engine 10.

A duct 18 is located below the cylinder head 16 in the combustion chamber 30. Specifically, the duct 18 is entirely located within a volume of the combustion chamber 30. Alternatively, the duct 18 is partially located with the combustion chamber 30 and inside the cylinder head 16. The portion of the duct 18 located in the combustion chamber 30 may be configured with one or more air passages for mixing fuel from the fuel injector 66 with combustion chamber gases, as will be described below in FIGS. 2A, 2B, and 2C. In some examples, additionally or alternatively, the duct 18 may be omitted and the injector 66 may extend through the cylinder head 16 and into the combustion chamber 30. A portion of the injector 66 located in the combustion chamber 30 below the cylinder head 16 may be machined with air passages for mixing fuel from the fuel injector 66 with combustion chamber gases, as will be described below in FIG. 3.

The cylinder walls 32, piston 36, and cylinder head 16 may thus form the combustion chamber 30, where a top surface 17 of the piston 36 serves as the bottom wall of the combustion chamber 30 while an opposed surface or fire deck 19 of the cylinder head 16 forms the top wall of the combustion chamber 30. Thus, the combustion chamber 30 may be the volume included within the top surface 17 of the piston 36, cylinder walls 32, and fire deck 19 of the cylinder head 16.

Fuel injector 66 may be positioned to inject fuel directly into combustion chamber 30, which is known to those skilled in the art as direct injection. Specifically, the fuel injector 66 is positioned to inject fuel directly into the portion of the duct 18 located in the combustion chamber 30. Thus, fuel may flow from the injector 66 through the duct 18, and then into the combustion chamber 30. Fuel injector 66 delivers liquid fuel in proportion to the pulse width of signal FPW from controller 12. Fuel is delivered to fuel injector 66 by a fuel system (not shown) including a fuel tank, fuel pump, and fuel rail. Fuel injector 66 is supplied operating current from driver 68 which responds to controller 12. In some examples, the engine 10 may be a diesel engine, and the fuel tank may include diesel fuel, which may be injected by injector 66 into the combustion chamber 30. However, in other examples, the engine 10 may be a gasoline engine, and the fuel tank may include gasoline fuel, which may be injected by injector 66 into the combustion chamber. Further, in such examples where the engine 10 is configured as a gasoline engine, the engine 10 may include a spark plug to initiate combustion in the combustion chamber 30.

In some examples, duct 18 may be included to reduce the temperature of air that is entrained by the fuel injected from the injector 66. Specifically, when fuel exits the injector 66 during fuel injection, it may travel a distance while mixing with air in the duct 18 before combusting. In the description herein, the distance the fuel spray travels before combusting may be referred to as the "lift-off length." In particular, the lift-off length may refer to the distance the injected fuel travels before the combustion process begins. Thus, the lift-off length may be a distance between an orifice of the injector 66 from which the fuel exits the injector 66, to a point in the combustion chamber 30 at which combustion of the fuel occurs.

The duct 18 may decrease the temperature of the gases that mix with the fuel prior to combustion in the combustion chamber 30. In this way, the lift-off length of the fuel spray may be increased and/or an amount of air entrainment in the fuel spray may be increased. The duct 18 may be positioned inside of and in fluidic communication with combustion chamber 30, such that gases in the combustion chamber 30 may enter the mixing passages of the duct 18 and be recirculated back into the combustion chamber 30. As one example, intake air introduced into the combustion chamber 30 during an intake stroke, may be pushed into the duct 18 during all or a portion of the compression stroke. In further examples, the duct 18 may be partially positioned exterior to the combustion chamber 30, such that at least a portion of the mixing passage 18 may be positioned within the combustion chamber 30 and a remaining portion may be positioned outside the combustion chamber 30 in the cylinder head 16.

In some examples, such as in the example of FIG. 1, the duct 18 may be positioned vertically below the cylinder head 16 with respect to the ground when coupled in an on-road vehicle. In some examples, substantially all of the duct 18 may be positioned exterior to the cylinder head 16 such that no portion of the duct 18 extends into the cylinder head 16. However, in other examples, a portion of the duct 18 may extend into the cylinder head 16.

In some examples, such as the example shown in FIG. 1, the duct 18 may be positioned between one or more outlets of the fuel injector 66 and the combustion chamber 30. Thus, fuel injected by the injector 66 may pass through the duct 18, before entering the combustion chamber 30. In particular, the injector 66, may be coupled to a top of the duct 18, where the mixing passages of the duct 18 are open to the combustion chamber 30. For example, as depicted below with reference to FIGS. 2A and 2C, the top and/or upper portion of the duct 18 may be pressed against the fire deck 19 of the cylinder head 16, and/or may integrally form a portion of the fire deck 19. As such, fuel may be injected from the injector 66, and may exit the injector 66, from a position vertically above the combustion chamber 30 and cylinder block 14, and vertically above the fire deck 19 of the cylinder head 16.

A glow plug may additionally be included to heat fuel injected by the fuel injector 66 to increase combustion during for example, an engine start or engine cold start. In some examples, such as examples where the duct 18 is included between the fuel injector 66 and the combustion chamber 30, the glow plug may be coupled to the duct 18, and may extend into the duct 18. In other examples, the glow plug may be coupled to the combustion chamber 30, and may extend into the combustion chamber 30.

Intake manifold 144 is shown communicating with optional electronic throttle 62 which adjusts a position of throttle plate 64 to control airflow to engine cylinder 30. This may include controlling airflow of boosted air from intake boost chamber 146. In some embodiments, throttle 62 may be omitted and airflow to the engine may be controlled via a single air intake system throttle (AIS throttle) 82 coupled to air intake passage 42 and located upstream of the intake boost chamber 146. In yet further examples, throttle 82 may be omitted and airflow to the engine may be controlled with the throttle 62.

In some embodiments, engine 10 is configured to provide exhaust gas recirculation, or EGR. When included, EGR may be provided as high-pressure EGR and/or low-pressure EGR. In examples where the engine 10 includes low-pressure EGR, the low-pressure EGR may be provided via EGR passage 135 and EGR valve 138 to the engine air intake system at a position downstream of air intake system (AIS) throttle 82 and upstream of compressor 162 from a location in the exhaust system downstream of turbine 164. EGR may be drawn from the exhaust system to the intake air system when there is a pressure differential to drive the flow. A pressure differential can be created by partially closing AIS throttle 82. Throttle plate 84 controls pressure at the inlet to compressor 162. The AIS may be electrically controlled and its position may be adjusted based on optional position sensor 88.

Ambient air is drawn into combustion chamber 30 via intake passage 42, which includes air filter 156. Thus, air first enters the intake passage 42 through air filter 156. Compressor 162 then draws air from air intake passage 42 to supply boost chamber 146 with compressed air via a compressor outlet tube (not shown in FIG. 1). In some examples, air intake passage 42 may include an air box (not shown) with a filter. In one example, compressor 162 may be a turbocharger, where power to the compressor 162 is drawn from the flow of exhaust gases through turbine 164. Specifically, exhaust gases may spin turbine 164 which is coupled to compressor 162 via shaft 161. A wastegate 72 allows exhaust gases to bypass turbine 164 so that boost pressure can be controlled under varying operating conditions. Wastegate 72 may be closed (or an opening of the wastegate may be decreased) in response to increased boost demand, such as during an operator pedal tip-in. By closing the wastegate, exhaust pressures upstream of the turbine can be increased, raising turbine speed and peak power output. This allows boost pressure to be raised. Additionally, the wastegate can be moved toward the closed position to maintain desired boost pressure when the compressor recirculation valve is partially open. In another example, wastegate 72 may be opened (or an opening of the wastegate may be increased) in response to decreased boost demand, such as during an operator pedal tip-out. By opening the wastegate, exhaust pressures can be reduced, reducing turbine speed and turbine power. This allows boost pressure to be lowered.

However, in alternate embodiments, the compressor 162 may be a supercharger, where power to the compressor 162 is drawn from the crankshaft 40. Thus, the compressor 162 may be coupled to the crankshaft 40 via a mechanical linkage such as a belt. As such, a portion of the rotational energy output by the crankshaft 40, may be transferred to the compressor 162 for powering the compressor 162.

Compressor recirculation valve 158 (CRV) may be provided in a compressor recirculation path 159 around compressor 162 so that air may move from the compressor outlet to the compressor inlet so as to reduce a pressure that may develop across compressor 162. A charge air cooler 157 may be positioned in boost chamber 146, downstream of compressor 162, for cooling the boosted aircharge delivered to the engine intake. However, in other examples as shown in FIG. 1, the charge air cooler 157 may be positioned downstream of the electronic throttle 62 in an intake manifold 144. In some examples, the charge air cooler 157 may be an air to air charge air cooler. However, in other examples, the charge air cooler 157 may be a liquid to air cooler.

In the depicted example, compressor recirculation path 159 is configured to recirculate cooled compressed air from downstream of charge air cooler 157 to the compressor inlet. In alternate examples, compressor recirculation path 159 may be configured to recirculate compressed air from downstream of the compressor and upstream of charge air cooler 157 to the compressor inlet. CRV 158 may be opened and closed via an electric signal from controller 12. CRV 158 may be configured as a three-state valve having a default semi-open position from which it can be moved to a fully-open position or a fully-closed position.

Universal Exhaust Gas Oxygen (UEGO) sensor 126 is shown coupled to exhaust manifold 148 upstream of emission control device 70. Emission control device may be a catalytic converter and as such may also be referred to herein as catalytic converter 70. Alternatively, a two-state exhaust gas oxygen sensor may be substituted for UEGO sensor 126. Converter 70 can include multiple catalyst bricks, in one example. In another example, multiple emission control devices, each with multiple bricks, can be used. Converter 70 can be a three-way type catalyst in one example. While the depicted example shows UEGO sensor 126 upstream of turbine 164, it will be appreciated that in alternate embodiments, UEGO sensor may be positioned in the exhaust manifold downstream of turbine 164 and upstream of convertor 70.

In some examples, a diesel particulate filter (DPF) 74 may be coupled downstream of the emission control device 70 to trap soot. The DPF 74 may be manufactured from a variety of materials including cordierite, silicon carbide, and other high temperature oxide ceramics. The DPF 74 may be periodically regenerated in order to reduce soot deposits in the filter that resist exhaust gas flow. Filter regeneration may be accomplished by heating the filter to a temperature that will burn soot particles at a faster rate than the deposition of new soot particles, for example, 400-600° C.

However, in other examples, due to the inclusion of duct 18 and/or mixing passages in a nozzle of the fuel injector 66, DPF 74 may not be included in the engine 10. Thus, by including the duct 18, an amount of air entrained by the fuel in the duct 18 prior to combustion in the combustion chamber 30 is increased. As such soot production during the combustion cycle may be reduced. In some examples, soot levels may be reduced to approximately zero due to the increased commingling of fuel and air prior to combustion/ignition of the mixture in the combustion chamber 30. As such, approximately no soot (e.g., zero soot) may be produced by engine 10 during the combustion cycle in some examples. In other examples, due to the inclusion of duct 18, soot production may be reduced and as such, the DPF 74 may be regenerated less frequently, reducing fuel consumption.

During the combustion cycle, each cylinder within engine 10 may undergo a four stroke cycle including: an intake stroke, compression stroke, power stroke, and exhaust stroke. During the intake stroke and power stroke, the piston 36 moves away from the cylinder head 16 towards a bottom of the cylinder increasing the volume between the top of the piston 36 and the fire deck 19. The position at which piston 36 is near the bottom of the cylinder and at the end of its intake and/or power strokes (e.g., when combustion chamber 30 is at its largest volume) is typically referred to by those of skill in the art as bottom dead center (BDC). Conversely, during the compression and exhaust strokes, the piston 36 moves away from BDC towards a top of the cylinder (e.g., fire deck 19), thus decreasing the volume between the top of the piston 36 and the fire deck 19. The position at which piston 36 is near the top of the cylinder and at the end of its compression and/or exhaust strokes (e.g., when combustion chamber 30 is at its smallest volume) is typically referred to by those of skill in the art as top dead center (TDC). Thus, during the intake and power strokes, the piston 36 moves from TDC to BDC, and during the compression and exhaust strokes, the piston 36 moves from BDC to TDC.

Further, during the intake stroke, generally, the exhaust valves 154 close and the intake valves 152 open to admit intake air into the combustion chamber 30. During the compression stroke, both valves 152 and 154 may remain closed, as the piston 36 compresses the gas mixture admitted during the intake stroke. During the compression stroke, gases in the combustion chamber 30 may be pushed into the duct 18 due to the positive pressure created by the piston 36 as it travels towards the duct 18. The gases from the combustion chamber 30 may dissipate heat through one or more of the cylinder head 16 and ambient air via conduction and/or convention. As such, the temperature of the gases in the duct 18 may be reduced relative to the temperature of the gases in the combustion chamber 30.

When the piston 36 is near or at TDC during the compression and/or power stroke, fuel is injected into the combustion chamber 30 by injector 66. During the ensuing power stroke, the valves 152 and 154 remain closed, as the expanding and combusting fuel and air mixture pushes the piston 36 towards BDC. In some examples, fuel may be injected prior to the piston 36 reaching TDC, during the compression stroke. However, in other examples, fuel may be injected when the piston 36 reaches TDC. In yet further examples, fuel may injected after the piston 36 reaches TDC and begins to translate back towards BDC during the power stroke. In yet further examples, fuel may be injected during both the compression and power strokes.

Fuel may be injected over a duration. An amount of fuel injected and/or the duration over which fuel is injected may be varied via pulse width modulation (PWM) according to one or more linear or non-linear equations. Further, the injector 66 may include a plurality of injection orifices, and an amount of fuel injected out of each orifice may be varied as desired.

The injected fuel travels through a volume of the duct 18 before entering the combustion chamber 30. Said another way, the duct 18 includes air passages and fuel passages for entraining air and fuel, wherein the passages are located inside the combustion chamber 30. However, the passages are defined by surfaces of the duct 18 and fuel and air flow through these passages before flowing outside of the duct 18 and into the combustion chamber 30 to mix with unmixed combustion chamber gases. The flow of air and fuel through the duct 18 will be described in greater detail below. It will be appreciated that the same phenomenon may occur if the duct is omitted and passages are integrated into a nozzle of the fuel injector 66 instead.

During the exhaust stroke, the exhaust valves 154 may open to release the combusted air-fuel mixture to exhaust manifold 148 and the piston 36 returns to TDC. Exhaust gases may continue to flow from the exhaust manifold 148, to the turbine 164 via exhaust passage 180.

Both the exhaust valves 154 and the intake valves 152 may be adjusted between respective closed first positions and open second positions. Further, the position of the valves 154 and 152 may be adjusted to any position between their respective first and second positions. In the closed first position of the intake valves 152, air and/or an air/fuel mixture does not flow between the intake manifold 144 and the combustion chamber 30. In the open second position of the intake valves 152, air and/or an air/fuel mixture flows between the intake manifold 144 and the combustion chamber 30. In the closed second position of the exhaust valves 154, air and/or an air fuel mixture does not flow between the combustion chamber 30 and the exhaust manifold 148. However, when the exhaust valves 154 is in the open second position, air and/or an air fuel mixture may flow between the combustion chamber 30 and the exhaust manifold 148.

Note that the above valve opening and closing schedule is described merely as an example, and that intake and exhaust valve opening and/or closing timings may vary, such as to provide positive or negative valve overlap, late intake valve closing, or various other examples.

Controller 12 is shown in FIG. 1 as a microcomputer including: microprocessor unit 102, input/output ports 104, read-only memory 106, random access memory 108, keep alive memory 110, and a conventional data bus. Controller 12 is shown receiving various signals from sensors coupled to engine 10, in addition to those signals previously discussed, including: engine coolant temperature (ECT) from temperature sensor 112 coupled to cooling sleeve 114; a position sensor 134 coupled to an input device 130 for sensing input device pedal position (PP) adjusted by a vehicle operator 132; a knock sensor for determining ignition of end gases (not shown); a measurement of engine manifold pressure (MAP) from pressure sensor 121 coupled to intake manifold 144; a measurement of boost pressure from pressure sensor 122 coupled to boost chamber 146; an engine position sensor from a Hall effect sensor 118 sensing crankshaft 40 position; a measurement of air mass entering the engine from sensor 120 (e.g., a hot wire air flow meter); and a measurement of throttle position from sensor 58. Barometric pressure may also be sensed (sensor not shown) for processing by controller 12. Pre-mature combustion may be sensed by a photodiode 92 measuring lumens in the duct 18 for processing by controller 12. In a preferred aspect of the present description, Hell effect sensor 118 produces a predetermined number of equally spaced pulses every revolution of the crankshaft from which engine speed (RPM) can be determined. The input device 130 may comprise an accelerator pedal and/or a brake pedal. As such, output from the position sensor 134 may be used to determine the position of the accelerator pedal and/or brake pedal of the input device 130, and therefore determine a desired engine torque. Thus, a desired engine torque as requested by the vehicle operator 132 may be estimated based on the pedal position of the input device 130.

The controller 12 receives signals from the various sensors of FIG. 1 and employs the various actuators of FIG. 1 to adjust engine operation based on the received signals and instructions stored on a memory of the controller. For example, adjusting cylinder temperatures based on a sensed light being greater than a threshold light may include adjusting an amount of EGR flowing to the engine 10. For example, EGR valve 138 may be moved closer to the fully open position. In one example, the threshold light is based on an amount of light corresponding to pre-ignition in the duct 18. As such, the mixture of fuel and air in the duct 18 is too hot and capable of igniting prior to flowing to the combustion chamber. In this way, soot formation may be greater than a desired value. Adjusting the amount of the EGR injection may include increasing the amount of EGR to decrease combustion chamber temperatures which may alleviate pre-ignition in the duct 18.

Thus, a system comprises a fuel injector comprising a nozzle tip submerged into a combustion chamber below a cylinder head, the nozzle tip comprising one or more fuel injection orifices configured to inject at an angle relative to a central axis of the fuel injector, and one or more mixing passages configured to receive a fuel injection or combustion chamber gases, where the one or more mixing passages configured to receive the fuel injection are oblique to the central axis and are aligned with the fuel injection orifices, and where the one or more mixing passages configured to receive combustion chamber gases include passage perpendicular to and parallel to the central axis, where the one or more mixing passage configured to receive the fuel injection are configured to receive combustion chamber gases from the one or more mixing passages configured to receive combustion chamber gases via one or more of a venturi passage and a louver.

The one or more mixing passages are integrated into the nozzle tip and are configured to receive combustion chamber gases include upper passages arranged perpendicularly to the central axis and lower passages arranged parallel to the central axis, and where the lower passages are further away from the cylinder head than the upper passages. Each of the one or more mixing passages configured to receive the fuel injection are located between the upper and lower passages, and where the one or more passages configured to receive the fuel injection increase in diameter at an intersection where the upper and lower passages are fluidly coupled to the one or more passages configured to receive the fuel injection.

Additionally or alternatively, the one or more mixing passages configured to receive combustion chamber gases include a first mixing passage arranged adjacent to the cylinder head and a second mixing passage arranged distal to the cylinder head, where the first mixing passage is perpendicular to the central axis and the second passage is parallel to the central axis, and where the one or more mixing passages configured to receive the fuel injection include a third mixing passage arranged angled to the central axis and located between the first and second mixing passages. The first, second, and third mixing passages are integrated into a cylindrical duct, where a portion of the duct is coupled to the fuel injector in the cylinder head and where a remaining portion of the duct comprising the mixing passages is below the cylinder head.

FIGS. 2A-2C include an axis system 290 which may be used to describe the relative positioning of components of the engine system. The axis system 290 may include a vertical axis 292, a lateral axis 294, and a longitudinal axis 296. The axes 292, 294, and 296 may be orthogonal to one another, thereby defining a three-dimensional axis system. As used herein, "top/bottom", "upper/lower", and "above/below", may be relative to the vertical axis 292 and may be used to describe the positioning of elements of the figures relative to one another along the vertical axis 292. Thus, a first component described as "vertically above" a second component may be positioned vertically above the second component relative to the vertical axis 292 (e.g., in a positive direction along axis 292 relative to the second component). Similarly, "to the left/right of," and "to the side of" may be used to describe the positioning of elements of the figures relative to one another along the lateral axis 294 and may be used to describe the positioning of elements of the figures relative to one another along the lateral axis 294.

Focusing on FIG. 2A, it shows a side cross-sectional view 200 of the injector 66, which may be included in engine 10, described above with reference to FIG. 1. As depicted in FIG. 2A, duct 18 is physically coupled to a nozzle 212 extending from an injector body 210 of the fuel injector 66. The portion of the duct 18 above the cylinder head 16 is coupled to the head via a boss, press fit, screws, clips, fusions, and/or welds. As such, the duct 18 is hermetically sealed to the cylinder head 16 such that pressurized contents in the cylinder do not flow through the coupling between the duct 18 and the cylinder head 16. In this way, portions of the duct 18 outside of the combustion chamber 30 and in the cylinder head 16 do not receive combustion chamber gases.

Additionally or alternatively, the duct 18 may be located completely below the cylinder head 16. As such, a top of the duct 18 is flush with fire deck 19 of the cylinder head 16. It will be appreciated that the duct 18 may be coupled to the fire deck 19 via any of the coupling elements described above. Additionally, the duct 18 pressed against the fire deck 19 to form a hermetic seal preventing the passage of gases and liquids.

The duct 18 is cylindrical, in one example. As such, a diameter of the duct 18 is uniform for its entire height. It will be appreciated that the duct 18 may be other shapes without departing from the scope of the present disclosure. For example, the duct 18 may be frustoconical, cubical, trigonal pyramidal, etc.

Fire deck 19 represents a lowest portion of the cylinder head 16 relative to the vertical axis 292. Thus, the fire deck 19 is a surface of the cylinder head 16 facing the combustion chamber 30. Furthermore, combustion chamber gases may come into contact with the fire deck 19. As described above, a volume of the combustion chamber 30 is limited by the cylinder head 16, a piston (e.g., piston 36 of FIG. 1), and cylinder side walls (e.g., cylinder side walls 32 of FIG. 1). The volume of the combustion chamber 30 includes at least a portion of the duct 18, if not an entirety of the duct 18. However, while the volume of the combustion chamber 30 is adjustable via the piston, a volume of the duct 18 is fixed and does not change. As such, when the piston is in a TDC position, it is closest to the duct 18 and the combustion chamber 30 is at a smallest volume. Alternatively, when the piston is in a BDC position, it is furthest from the duct 18 and the combustion chamber 30 is at a largest volume. Thus, the duct 18 is positioned vertically above a piston (e.g., piston 36 of FIG. 1) during the entire combustion cycle, such that the duct 18 is vertically above the piston at TDC and BDC, and any position there-between. As such, the duct 18 is positioned vertically above the piston and does not contact the piston at TDC, BDC, and any position there-between.

The duct 18 and injector 66 are aligned on a central axis 298, which is parallel to the vertical axis 292 and a direction of movement of the piston. In this way, the central axis 298 may pass through geometric centers of the piston, fuel injector 66, and duct 18. It will be appreciated that in some embodiments, the fuel injector 66 and duct 18 may not be aligned with a center of the piston. As such, the injector 66 and duct 18 may be in a different radial location of the cylinder head 16. Alternatively, the injector 66 and duct 18 may be positioned obliquely in the cylinder head 16 and combustion chamber 30.

The duct 18 includes mixing passages 230 located below the cylinder head 16. In this way, combustion chamber gases may flow in and out of the mixing passages 230 without flowing out of the combustion chamber 30. The mixing passages 230 include first mixing passages 232, second mixing passages 234, and third mixing passages 236. As shown, a plurality of first mixing passages 232 are located around a circumference of the duct 18 adjacent the cylinder head 16. A single second mixing passage 234 is located in the duct 18 along the central axis 298.

The first 232 and second 234 mixing passages are misaligned with fuel injection orifices of the nozzle 212. In this way, the first 232 and second 234 mixing passages are configured to only receive combustion chamber gases and do not receive fuel injections 250. As shown, fuel injections 250 are ejected from the fuel injection orifices located on a portion of the nozzle 212 extending into the combustion chamber 30 below the cylinder head 16. The third mixing passages 236 are aligned with the fuel injection orifices of the nozzle 212 and receive the fuel injections 250.

Below the cylinder head 202, the duct 18 includes mixing passages 230. Specifically, the mixing passages 230 include a plurality of first mixing passages 232 and a second mixing passage 234. The first mixing passages 232 are radially spaced around the duct 18. The first mixing passage 232 form an angle between 60 to 90 degrees relative to the central axis 298. In one example, the first mixing passages 232 are exactly perpendicular to the central axis 298. The second mixing passage 234 forms an angle between 0 to 30 degrees relative to the central axis 298. In one example, the second mixing passage 234 is a single passage parallel to the central axis 298. In this way, the first mixing passages 232 are directed toward cylinder walls and second mixing passage 234 is directed toward a piston. A plurality of third mixing passages 236 are located between the first 232 and second 234 mixing passages. In one example, a number of third mixing passages 236 is substantially equal to a number of first mixing passages 232. The third mixing passages 236 receive fuel injections 250 from the nozzle 212, while combustion chamber gases flow through the first 232 and second 234 mixing passages. The combustion chamber gases and fuel injections 250 may mix in the third mixing passages 236 before the fuel injections 250 exit the third mixing passages 236 and flow into the combustion chamber 30. In this way, the fuel injections 250 mix with combustion chamber gases in the third mixing passages 236 before combining with unmixed combustion chamber gases in the combustion chamber 30.

Although the duct 18 is shown in segmented portion in the cross-sectional view 200, the duct 18 is cylindrical with a plurality of first mixing passages 232 located around a circumference of the duct 18 proximal to the cylinder head 202 and a second mixing passage 234 located below the first mixing passages 232 along a center of the duct 18 parallel to the vertical axis 290. In this way, the first mixing passages 232 are orthogonal to the second mixing passage 234.

White head filled arrows show an example flow of combustion chamber gases in the duct 18. As shown, combustion chamber gases flow through the first 232 and second 234 mixing passages and enter the third mixing passage 236 at a location near the nozzle 212. Additionally or alternatively, the mixing passages 230 may comprise one or more mixing features to increase combustion chamber gas entrainment with the fuel injections 250 prior to fuel flowing out of the duct 18 and into the combustion chamber 30.

As described above, the mixing passages 230 of the duct 18 are located within a volume of the combustion chamber 30. The mixing passages 230 and the combustion chamber 30 may be described as two separated volumes of spaces fluidly coupled to one another, where fuel mixed with combustion gases flows from the third mixing passage 236 into the combustion chamber 30, where combustion gases having a lower amount of fuel reside.

Turning now to FIG. 2B, it shows an embodiment 215 of the third mixing passage 236 of the duct 18. As shown, the third mixing passage 236 is aligned with an injection orifice 271 of the nozzle 212. A gap 274 is located between the third mixing passage 236 and the injection orifice 271. Due to the high velocity and pressure of the fuel injection 250, substantially all of the fuel injection enters the third mixing passage 236 and does not escape through the gap 274 to a remainder of the duct 18. However, the gap 274 fluidly couples the third mixing passage 236 to the first 232 and second 234 mixing passages. The fuel injection 250 may create a vacuum in the gap 274 once it enters the third mixing passage 236, wherein combustion chamber gases from the first 232 and second 234 mixing passages are drawn into the gap 274 and directed into the third mixing passage 236 to be entrained with the fuel injection 250.

The third mixing passage 236 further comprises a venturi feature 251. The venturi feature 251 comprising a venturi inlet 252, a venturi outlet 254, and a venturi throat 256. The venturi throat 256 comprises orifices 258 for fluidly coupling the third mixing passage 236 to one or more of the first 232 and second 234 mixing passages. As the fuel injection 250 flows through the venturi throat 256, vacuum is supplied through the orifices 258 to either the first 232 or second 234 mixing passages. Thus, combustion chamber gases are drawn through the orifices 258 to the venturi throat 256. In this way, the third mixing passage 236 may receive air (e.g., combustion chamber gases) adjacent the cylinder head 16 via the gap 274 and distal the cylinder head 16 via the orifices 258. In one example, a number of orifices is substantially equal to two, with a first orifice fluidly coupling the third mixing passage 236 to the first mixing passage 232 and a second orifice fluidly coupling the third mixing passage 236 to the second mixing passage 234.

Additionally, a surface 237 of the third mixing passage 236 comprises first surface features 260. The first surface features 260 may extend inward towards a center of the third mixing passage 236. The surface features 260 may therefore disturb laminar flow within the third mixing passage 236 and may increase turbulence of the fuel injection 250 and/or combustion chamber gases.

As another example, one or more second surface features 262 may be included along the interior of the surface 237 of the third mixing passage 236. The second surfaces features 262 may include one or more grooves 263 that may increase the roughness of the surface 237 of the third mixing passage 236. In this way, viscous drag forces exerted by the surface 237 on the fuel injection 250 and/or combustion chamber gases entering through the gap 274 may be increased by the inclusion of the groves 263, and thus the turbulent boundary layer thickness may be increased, enhancing mixing of the fuel and air prior to delivery to the combustion chamber 30.

Turning to FIG. 2C, it shows a second embodiment 217 of the third mixing passage 236, which is substantially identical to the first embodiment 215, except that the second embodiment 217 comprises a louver 270 instead of the venturi feature 251. The louver 270 comprises a louver inlet 272, which narrows toward a louver throat 276, similar to the venturi inlet 252. The louver inlet 272 comprises two angled protrusions which reduce a diameter of the third mixing passage 236. As a fluid (e.g., fuel injection 250 or combustion chamber gases flow through the inlet 272 and into a louver outlet 276, vacuum is generated in the louver throat 276. As shown, the louver outlet 276 is a constant diameter substantially equal to a largest diameter of the third mixing passage 236, where the venturi outlet 254 increases in diameter in a downstream direction relative to a direction of fuel injection flow. As such, orifices 278 draw combustion chamber gases from the first 232 and/or second 234 mixing passages and direct the gases to the louver throat 276. As such, the second embodiment 217 of the third mixing passage 236 may function similarly to the first embodiment 215 of the third mixing passage 236.

In this way, the fuel injection 250 may mix with combustion chamber gases upstream of the venturi inlet 252 and at the venturi throat 256. The venturi and/or louver elements enable fuel/air mixing prior to exiting the duct 18. Soot production may be substantially decreased and/or prevented by mixing fuel and combustion gases in the third mixing passage 236. During some engine operating conditions, where a temperature of the mixture of the fuel injection 250 and combustion chamber gases exceeds a threshold temperature and combusts prematurely, soot production may be greater than a desired amount. Premature combustion may be defined as combustion occurring within the duct 18. As such, light may be released in the duct 18, where a light sensor (e.g., light sensor 92 of FIG. 1) may detect the premature combustion and adjust one or more engine operating parameters, as will be described below in the method of FIG. 4.

The duct shown may be operated in conjunction with the method of FIG. 4, which comprises flowing combustion chamber gases into first and second passages located below a cylinder head, injecting fuel from a fuel injector to a third passage located below a cylinder head in a combustion chamber, the third passage being fluidly coupled to the first and second passages, mixing the fuel with combustion chamber gases before flowing the fuel from the passage to the combustion chamber, and adjusting one or more of an EGR flow rate, intake manifold pressure and temperature, and in-cylinder water injection in response to a sensed amount of light generated in the passage being greater than a threshold light. The first, second, and third passages are integrated into a duct configured to be coupled to the fuel injector. The first, second, and third passages are integrated into a nozzle tip of the fuel injector. The third passage further comprises a venturi passage fluidly coupling the third passage to the first passage and the second passage. The first, second, and third passages are located entirely below the cylinder head such that combustion chamber gases do not flow into the cylinder head.

Turning now to FIG. 3, it shows an embodiment 300 of a nozzle tip 310 configured to entrain combustion chamber gases. In one example, the nozzle tip 310 may be integrated into a nozzle (e.g., nozzle 212 of fuel injector 66 of FIG. 2A) and function similarly to duct 18. As such, the nozzle with the nozzle tip 310 does not comprise the duct 18. As such, mixing passages 330 are integrated into the nozzle tip 310. In one example, the mixing passages 330 may function similarly to the mixing passages 230 of FIG. 2A.

Mixing passages 330 comprise a first passage 332 fluidly coupled to second passages 334 and third passage 336. The first passage 332 is configured to receive a fuel injection from a fuel injection orifice of the nozzle tip 310. As such, the first passage 332 is aligned with the fuel injection orifice along its central axis 390. The first passage 332 occupies a space between the fuel injection orifice and the line 392, which is perpendicular to the central axis 390.

Below the line 392, the mixing passages 330 trifurcate into namely, two second passages 334 oblique to the central axis 390 and line 392 and into the third passage 336 parallel to the central axis 390 and perpendicular to the line 392. The third passage 336 is configured to readily receive the fuel injection from the first passage 336. However, as shown, the third passage 336 is wider than the first passage 332. In one example, a radius of the third passage 336 is greater than a radius of the first passage 332 by a distance 342. This allows a fuel injection to flow through the first passage 332 and into the third passage 336 without entering the second passages 334. As shown, the third passage 336 extends from the line 392 to the combustion chamber 30, thereby expelling the fuel injection received from the first passage 332 to the combustion chamber 30.

The second passages 334 extends from the combustion chamber 30 at a location distal to the central axis 390 to an intersection 350 the third passage 336 and line 392, where the intersection is proximal to the central axis 390. As such, the second passages 334 are slanted and/or angled. In one example, the second passages 334 are at a 45° angle relative to the central axis 390 and the line 392. Additionally or alternatively, the second passages 334 may be less angled (e.g., angle less than 45°) to the central axis 390. Each of the second passages 334 comprises a first opening 352 with a height 344 at the intersection 350. Additionally, each of the second passages 334 comprises a second opening 354 at a lowest portion of the nozzle tip 310 adjacent the combustion chamber 30.

A number of first passages 332 is substantially equal to a number of fuel injection orifices. Likewise, a number of third passages 336 is substantially equal to the number of first passage 332. In one example, there are two second passages 334 for each third passage 336. It will be appreciated that there may be less than or greater than two second passages 334 for each third passage 336 without departing from the scope of the disclosure.

Combustion chamber gases flow into each of the second passage 334 via the second opening 354, as shown by white head arrows. During engine operating conditions where a fuel injection is not occurring, combustion chamber gases may enter the first passage 332 and third passage 336 through an outlet 338. However, once the fuel injection flows through the first passage 332 and third passage 336, combustion chamber gases are forced out of the first 332 and third 336 passages due to a high pressure of the fuel injection. A general direction of flow of the fuel injection is shown by black head arrows. As such, the fuel injection flows in a direction substantially parallel to the central axis 390. Combustion chamber gases flow from each of the second passages 334, through the first opening 352, and into the third passage 336 as the fuel injection flows past the first openings. Additionally, due to the angle of the second passage 334, a direction of combustion chamber gas flow into the third passage 336 is oblique and/or perpendicular to a direction of fuel injection flow. As such, turbulence in the third passage 336 is increased. In one example, the flow of combustion chamber gases in the second 334 and third 336 passages is substantially V-shaped and the flow of the fuel injection in the first 332 and third 336 passages is substantially linear. In this way, the fuel injection mixes with combustion chamber gases before flowing through the outlet 338 and into the combustion chamber 30.

In this way, the nozzle tip 310 is fluidly coupled to combustion chamber 30 via a plurality of openings. Second openings 354 function as inlets, admitting combustion chamber gases into the second passage 334. Outlet 338 expels a mixture of a fuel injection and combustion chamber gases to the combustion chamber 30. The second openings 354 and outlet 338 may be a variety of sizes and/or shapes without departing from the scope of the present disclosure. For example, the openings may be oblong, circular, square, triangular, etc. By flowing combustion chamber gases and the fuel injection out of the third passage 336 together, soot formation is decreased and/or prevented.

In some embodiments, additionally or alternatively, the central axis 390 is oblique to a central axis of a fuel injector (e.g., fuel injector 66 of FIG. 1). As such, the second passages 334 are not angled similarly to the central axis of the fuel injector. In one example, a second passage on a left side of the figure is perpendicular to the central axis of the fuel injector and a second passage on a right side of the figure is parallel to the central axis of the fuel injector. In this way, the left second passage may be an upper second passage adjacent a cylinder head and the right second passage may be a lower second passage distal to the cylinder head. In this way, the upper and lower second passages may be substantially similar to the first 232 and second 234 passage of FIG. 2A. However, the passages differ in that mixing passages 330 are integrated into the nozzle tip 310, as shown in the embodiment of FIG. 3, and mixing passages 230 are integrated into a duct configured to couple to a nozzle, as shown in the embodiment of FIG. 2A. It will be appreciated that the surface features described above with respect to FIGS. 2B and 2C may be applied to the mixing passages of FIG. 3.

In one example, the nozzle tip 310 comprises three photodiodes, namely a first photodiode 372, a second photodiode 374, and a third photodiode 376. The photodiodes may be used similarly to photodiode 92 of FIG. 1. The first photodiode 372 is located adjacent to the first opening 352. The second photodiode 374 is located adjacent to the outlet 338. The third photodiode 376 is located on a cylinder facing surface of the nozzle tip 310. As such, the first photodiode 372 measures an amount of light near where combustion chamber gases and fuel initially mix. The second photodiode 374 measures an amount of light near a portion of the nozzle tip 310 where the mixture of fuel and combustion chamber leave the nozzle tip 310. Lastly, the third photodiode 376 measures an amount of light at an uppermost portion of the combustion chamber adjacent to the nozzle tip 310.

It will be appreciated that the first 372, second 374, and third 376 photodiodes may comprise different threshold light amounts. For example, the first photodiode 372 corresponds to a first threshold light, the second photodiode 374 corresponds to a second threshold light, and the third photodiode 376 corresponds to a third threshold light. In one example, the third threshold light is greater than the second threshold light, wherein the second threshold light is greater than the first threshold light. Thus, an amount of light exceeding the first threshold light may not exceed the second and third thresholds. As such, injection conditions in the nozzle tip 310 may be accordingly adjusted based on an amount of light exceeding the first threshold light. In one example, adjustments corresponding to an amount of light exceeding only one of the thresholds are less severe than adjustments corresponding to an amount of light exceeding all of the threshold lights. This will be described in greater detail below with respect to FIG. 4.

In one example, by including more than one photodiode, soot build-up in the nozzle tip may be diagnosed. Specifically, an amount and location of soot in the nozzle tip may be determined by an amount of light measured at a photodiode exceeding a corresponding threshold light. As such, operating parameters may be adjusted to burn the accumulated soot. For example, a fuel injection amount may decrease in response to the detection of accumulated soot, wherein the increased presence of oxygen may promote burning of the accumulated soot.

Additionally or alternatively, the photodiodes may not be included in the nozzle tip and/or a duct (e.g., duct 18). A fiber optic strand and/or light transmitting element may be located in the duct and/or nozzle tip and transmit light to a photodiode located in a different location (e.g., a cylinder wall).

Thus, FIGS. 1-3 show a system, comprising a fuel injector located in a cylinder head, a passage located below the cylinder head in a combustion chamber, the passage aligned with a fuel injector orifice of a nozzle of the fuel injector, and a controller with computer-readable instructions that when implemented allow the controller to decrease a cylinder temperature in response to an amount of light measured by a light sensor in the passage being greater than a threshold amount of light.

In one example, the passage is located in a duct, the duct being coupled to the cylinder head along a central axis of the fuel injector. The passage is a single passage of a plurality of mixing passages located on the duct, and where the mixing passages are fluidly coupled to one another, and where first and second passages of the mixing passages are misaligned with the fuel injector orifice and are angled to a direction of a fuel injection, and where third passages are aligned with each fuel injector orifice of the nozzle. The first passages extend in a radially outward direction perpendicular to the central axis of the fuel injector, the second passage extends in a vertical direction along the central axis of the fuel injector, and the third passages extend in a direction oblique to the central axis of the fuel injector. The third passages are located between the first and second passages.

In an alternative example, the passage is integrated into a tip of the nozzle. The passage is one or a plurality of passages including a first passage and a third passage aligned along a central axis of the fuel injector, and where a plurality of second passages are fluidly coupled to the third passage. The first and third passages direct a fuel injection toward the combustion chamber, and where the second passages direct combustion chamber gases to the third passage. The controller decreases the cylinder temperature by one or more of increasing an EGR flow rate, decreasing an intake manifold pressure and temperature, and increasing an in-cylinder water injection. The method of FIG. 4 further describes actions implemented by the controller in response to an amount of sensed light being greater than a threshold light.

Regardless, paths are machined into the duct, nozzle tip, and/or cylinder head to accommodate one or more photodiodes. Furthermore, electrical connections are integrated into the duct, nozzle tip, and/or cylinder head to provide communication pathways between the photodiode(s) and a controller (e.g., controller 12 of FIG. 1). It will be appreciated that the photodiodes may not be located inside the combustion chamber gases and fuel mixing paths, but instead may be located in surfaces of the duct, nozzle tip, and/or cylinder head. As such, a cutout allows the photodiode to visualize light emitted in the mixing paths without obstructing a flow path of the mixing paths.

Turning now to FIG. 4, it shows a method 400 for adjusting engine operating parameters in response to engine soot output. Instructions for carrying out method 400 may be executed by a controller based on instructions stored on a memory of the controller and in conjunction with signals received from sensors of the engine system, such as the sensors described above with reference to FIG. 1. The controller may employ engine actuators of the engine system to adjust engine operation, according to the methods described below.

At 402, the method 400 includes determining, estimating, and/or measuring current engine operating parameters. Current engine operating parameters may include, but are not limited to, one or more of manifold pressure, manifold temperature, throttle position, engine speed, engine temperature, coolant temperature, vehicle speed, EGR flow rate, and air/fuel ratio.

At 404, the method 400 includes measuring a light transmitted from a mixing passage, where the mixing passage is a passage of either a passage of a duct (e.g., third passage 236 of duct 18 of FIG. 2A) or a passage integrated into a nozzle tip (e.g., third passage 336 of FIG. 3). As described above, the passage may be configured with a photodiode adapted to measure an amount of light transmitted from the duct. An amount of light measured may be indicative of a degree of pre-ignition. Thus, when the amount of light increases, the degree of pre-ignition increases and may result in less than a desired amount of gas/fuel mixing. This may lead to increased soot formation compared to no pre-ignition occurring.

At 406, the method 400 includes determining if the light sensed by the photodiode is greater than a threshold amount of light. In one example, the threshold light is equal to an amount of light emitted from the duct corresponding to engine soot output being greater than a threshold soot output. In one example, the threshold soot output is equal to an emissions standard. In another example, the threshold soot output is equal to zero. If the sensed light is less than the threshold light, then engine soot output is less than the threshold soot output and the method 400 proceeds to 408 to maintain current engine operating parameters. In this way, engine soot output is relatively low and/or zero and engine operating parameters are not adjusted to reduce engine soot output.

If the light is greater than the threshold light, then too much pre-ignition is occurring and engine soot output is greater than the threshold soot output. The method 400 proceeds to 410 to adjust engine operating parameters.

In some embodiments, additionally or alternatively, the degree of pre-ignition is calculated based on feedback from one or more of a pressure transducer and strain gage in the duct. Additionally or alternatively, the calculation may further include feedback from an exhaust gas sensor located in an exhaust system. If excessive pressure (e.g., pressure greater than a threshold pressure), excessive strain (e.g., strain greater than a threshold strain), and/or excessive soot (e.g., soot greater than the threshold soot output) are detected, then too much pre-ignition is occurring and the method proceeds to 410. Each of the threshold pressure and threshold strain correspond to the same degree of pre-ignition as the threshold light.

At 410, the method 400 includes one or more of increasing EGR at 412, decreasing manifold pressure at 414, decreasing intake temperature at 416, increasing cooling in the area of the duct at 418, and increasing a water injection at 420. Increasing EGR at 412 may include adjusting an EGR valve to a more open position to allow a greater amount of EGR to flow to the intake passage. Decreasing a manifold pressure may include moving a throttle valve to a less open position. Additionally, EGR flow to the intake manifold may decrease to further decrease the intake manifold pressure. Additionally or alternatively, intake gases are directed through a charge air cooler (e.g., CAC 157 of FIG. 1) to further decrease the manifold pressure. Thus, EGR may still be increased at 412, but the EGR is directed through an EGR cooler prior to flowing to the intake manifold. Decreasing an intake temperature may include injecting water into an intake passage and/or manifold upstream of the combustion chamber. Increasing cooling in the area of the duct includes flowing coolant to portions of a cylinder cooling jacket proximal to the duct and/or nozzle tip. Increasing the water injection may include signaling to an actuator of a fuel injector located in-cylinder to injector a greater volume of water. Additionally or alternatively, an injection pressure is increased in response to the measured light being greater than the threshold light. In this way, the injection may flow into the combustion chamber more quickly than lower injection pressures, thereby mitigating a likelihood of pre-combustion.

In one example, the method may apply one or more of the adjustments at 410 based on a difference between the duct light transmitted and the threshold light. For example, if the difference is relatively high, then one or more of the adjustments may be employed. Additionally or alternatively, a magnitude of the adjustments is increased in response to the difference being relatively high. For example, an amount of the water injection is increased. Alternatively, if the difference is relatively low (e.g., less than the relatively high difference), then less of the adjustments may be employed. Additionally or alternatively, the magnitude of the adjustments is slightly increased or not increased at all. For example, an amount of the water injection is a baseline (e.g., lowest) amount. In this way, combustion chamber gases may include one or more of air, water, and/or EGR.

In this way, the method 400 adjusts engine operating parameters in response to light transmitted being greater than the threshold light. The engine operating parameters are adjusted to mitigate pre-ignition in the duct, which reduces the duct light transmitted. By doing this, fewer particulates, if any, are expelled through the exhaust valve to the exhaust manifold from the cylinder.

Additionally or alternatively, as described above in FIG. 3, multiple photodiodes may be included in the duct and/or nozzle tip. As such, the adjustments may be implemented based on one or more of a number of threshold lights being exceeding and a magnitude in which each of the threshold lights is exceeded. For example, if an amount of light measured exceeds the first threshold light and the second threshold light, but does not exceed the third threshold light, then the method 400 may inject water and decrease EGR flow. However, if an amount of light exceeds each of the first, second, and third threshold lights, then the method 400 may inject water, decrease EGR flow, and increase an injection pressure, in one example.

At 422, the method 400 includes flowing cylinder gas to mixing passages located in the duct. Prior to the injection, the cylinder gases may flow through any of the mixing passages located in the duct. However, due to the nature of the fuel injection, cylinder gases may only flow through the first and second mixing passages (e.g., first mixing passages 232 and second mixing passage 234, respectively, of FIG. 2A) of the duct before combining with the fuel injection and flowing through the outlet passage (e.g., outlet passage 236 of FIG. 2A). The cylinder gas is cooler following the adjustments at 410 described above compared to cylinder gas temperatures prior to the pre-ignition. In this way, pre-ignition in the duct is unlikely to occur.

At 424, the method 400 includes injecting and mixing fuel with cylinder gas in the duct. As described above, the fuel injection flows through a fuel conduit of the fuel injector before flowing out one or more injection orifices aligned with the one or more outlet passages. Cylinder gases from the first and second mixing passages flow into the outlet passages and mix with the fuel injection prior to exiting the outlet passages. This mixing may limit or prevent particulate matter from escaping the cylinder. In particular, an amount of fuel to be injected may be determined based on one or more of a driver demanded torque, a desired air/fuel ratio, mass airflow rate, etc. Further, the injection timing may be adjusted based on engine operating conditions. In particular, the fuel may be injected towards the combustion chamber. In some examples, the fuel may be injected substantially parallel to and/or in line with a fuel spray conduit of the mixing passage. Thus, the method 400 comprises mixing the injected fuel and the combustion chamber gases in the mixing passages inside the combustion chamber.

At 426, the method 400 includes directing the mixture including the fuel injection and cylinder gas to mix with unmixed cylinder gas. The unmixed cylinder gas may be defined as cylinder gas that is not mixed with fuel. The fuel/air mixture may flow into the combustion chamber during one or more of the compression stroke and/or power stroke.

At 428, the method 400 comprises igniting the fuel/air mixture in the combustion chamber. In some examples, the fuel/air mixture may spontaneously combust due to temperatures and pressure in the combustion chamber. In other examples, the fuel/air mixture may be ignited by a glow plug.

At 430, the method 400 includes ejecting the gasses in the combustion chamber during an exhaust stroke. In particular the method 400 may comprise opening one or more exhaust valves (e.g., exhaust valves 154 described above in FIG. 1) and ejecting the combustion chamber gasses to an exhaust manifold (e.g., exhaust manifold 148 described above in FIG. 1). The method 400 may comprise only ejecting the gases in the combustion chamber to the exhaust manifold during an exhaust stroke of the piston.

Turning now to FIG. 5, it shows an operating sequence 500 illustrating examples results for an engine having a controller (e.g., engine 10 and controller 12 of FIG. 1) implementing the method 400 of FIG. 4. Line 510 represents a cylinder gas temperature, line 520 represents a PM output temperature and line 522 represent a threshold PM output, line 530 represents an injection lift-off length and line 532 represents a threshold injection lift-off length, line 540 represents an amount of light measured and line 542 represents a threshold amount of light measured, line 550 represents an EGR flow rate, and line 560 represents if a water injection is occurring in the combustion chamber. The horizontal axes of each plot represent time and time increases from the left side of the figure to the right side of the figure.

Prior to $t_1$, a cylinder gas temperature and/or a combustion chamber gas temperature are relatively low, as shown by line 510. However, the cylinder gas temperature is increasing toward a high temperature. In one example, this is due to increasing engine load. As such, the injection lift-off begins to decrease from a relatively high length toward the threshold lift-off length, as shown by lines 530 and 532, respectively. The lift-off length decreases due to increasing combustion gas temperatures, which may result in an earlier combustion than desired. As such, PM output also begins to increase from a relatively low amount toward the threshold PM output, as shown by lines 520 and 522, respectively. As the lift-off length decreases, an amount of light measured by a light sensor in a duct and/or mixing passage increases toward the threshold amount of light measured, shown by lines 540 and 542, respectively. In one example, light sensor 92 of FIG. 1 is located in the second mixing passage 236 of FIGS. 2A, 2B, and 2C. In another example, the light sensor 92 of FIG. 1 is located in the third mixing passage 336 of FIG. 3. The threshold amount of light measured is substantially similar to the threshold light described at 406 in the method 400 of FIG. 4. Thus, combustion may occur in the duct or mixing passages before the fuel/combustion chamber gasses mixture flows into the combustion chamber when the light measured is greater than the threshold amount of light. An EGR flow rate is relatively low, as shown by line 550. A water injection is off, as shown by line 560.

At $t_1$, the cylinder gas temperature reaches a relatively high temperature. As a result, the PM output increases to a PM output greater than the threshold PM output. Additionally, the injection lift-off decreases to a lift-off length less than the threshold lift-off length. As such, light measured by the light sensor is greater than the threshold amount of light. Thus, combustion chamber temperatures are too high, resulting in premature combustion (e.g., burning) of fuel in either the duct (e.g., duct 18 of FIGS. 2A, 2B, and 2C) or in mixing passages integrated into a nozzle tip (e.g., mixing passages 330 of nozzle tip 310 of FIG. 3). In an effort to decrease the PM output and increase injection lift-off length, the EGR flow rate increases and the water injection is activated.

After $t_1$ and prior to $t_2$, the water injection continues and the EGR flow rate continues to increase toward a relatively high EGR flow rate to aid in decreasing cylinder gas temperatures. By doing this, the cylinder gas temperature decreases, and as a result the injection lift-off increases back toward the threshold lift-off, the PM output decreases toward the threshold PM output, and the light measured decreases toward the threshold amount of light measured.

At $t_2$, the cylinder gas temperature has sufficiently decreased such that the PM output decreases to a PM output less than the threshold PM output, the injection lift-off increases to an injection lift-off length greater than the threshold injection lift-off, and the light measured decreases to an amount of light less than the threshold amount of light measured. As such, the water injection is terminated and the EGR flow rate decreases. The water injection may be performed by an injector positioned to inject water into the combustion chamber in an area outside of and/or spaced away from the duct or nozzle tip. In some examples, additionally or alternatively, one or more of the water injection and EGR flow rate are maintained to maintain the cylinder gas temperature relatively low. This may be based on a combustion stability, EGR demand, and/or an amount of water available from a water reservoir fluidly coupled to an injector configured to inject into the cylinder.

After $t_2$, the cylinder gas temperature decreases to a relatively low temperature. The PM output is less than the threshold PM output. The injection lift-off is greater than the threshold injection lift-off. The lift measured is less than the threshold light measured. The EGR flow rate continues to decrease and the water injection remains deactivated.

Thus, FIG. 5 graphically illustrates a method comprising decreasing a combustion chamber temperature in response to an amount of light sensed in a passage fluidly coupling a fuel injector to the combustion chamber. The amount of light to a threshold light, the threshold light being based on light released in the passage when soot is produced above a desired amount. Decreasing the combustion chamber temperature includes flowing EGR to the combustion chamber, decreasing manifold pressure, decreasing an intake manifold temperature, and injecting water into the combustion chamber. Sensing the amount of light via a photodiode located in the passage. The method further includes mixing fuel with combustion chamber gases in the passage before flowing the fuel to the combustion chamber. The passage is located below a cylinder head, the passage is configured to direct a fuel injection into the combustion chamber.

In this way, a fuel injector may be fitted with mixing passages integrated into either a duct or a nozzle tip for entraining air a fuel injection. A portion of the passages align with fuel injection orifices and are configured to guide the fuel injection to the combustion chamber. A remaining portion of the passages receive combustion gases from the combustion chamber and guide the combustion gases to the passages receiving the fuel injection. The technical effect of mixing combustion gases with a fuel injection inside a passage before flowing the fuel injection to the combustion chamber is to decrease particulate matter output. By pre-mixing the fuel and combustion gas, pocket of unburned fuel may not form in the combustion chamber, which may not only increase fuel economy, but also prevent particulate matter output.

In an alternative embodiment, a method comprises flowing combustion chamber gases into first and second passages located below a cylinder head, injecting fuel from a fuel injector to a third passage located below a cylinder head in a combustion chamber, the third passage being fluidly coupled to the first and second passages, mixing the fuel with combustion chamber gases before flowing the fuel from the passage to the combustion chamber, and adjusting one or more of an EGR flow rate, intake manifold pressure and temperature, and in-cylinder water injection in response to a sensed amount of light generated in the passage being greater than a threshold light.

The first, second, and third passages are integrated into a duct configured to be coupled to the fuel injector. The first, second, and third passages are integrated into a nozzle tip of the fuel injector. The third passage further comprises a venturi passage fluidly coupling the third passage to the first passage and the second passage. The first, second, and third passages are located entirely below the cylinder head such that combustion chamber gases do not flow into the cylinder head.

One embodiment of a system comprises a fuel injector comprising a nozzle tip submerged into a combustion chamber below an end wall of a cylinder head, the nozzle tip comprising one or more fuel injection orifices configured to inject at an angle relative to a central axis of the fuel injector and one or more mixing passages configured to receive a fuel injection or combustion chamber gases, where the one or more mixing passages configured to receive the fuel injection are oblique to the central axis and are aligned with the fuel injection orifices, and where the one or more mixing passages are configured to receive combustion chamber gases. A first example of the system further includes where one or more mixing passages are integrated into the nozzle tip and are configured to receive combustion chamber gases and include upper passages and lower passages angled relative to a central axis, wherein the upper passages form an angle between 60-90 degrees with the central axis and the lower passages form an angle between 0-30 degrees with the central axis, and where the lower passages are further away from the cylinder head than the upper passages.

A second example of the system, optionally including the first example, further includes where each of the one or more mixing passages configured to receive the fuel injection are located between the upper and lower passages, and where the one or more passages configured to receive the fuel injection increase in diameter at an intersection where the upper and lower passages are fluidly coupled to the one or more passages configured to receive the fuel injection, and where one or more of the mixing passages comprises one or more of a venturi passage and a louver. A third example of the system, optionally including the first and/or second examples, further includes where the one or more mixing passages configured to receive combustion chamber gases include a first mixing passage arranged adjacent to the cylinder head and a second mixing passage arranged distal to the cylinder head, where the first mixing passage forms an angle relative to the central axis between 60 to 90 degrees and the second passage forms an angle relative to the central axis between 0 and 30 degrees, and where the one or more mixing passages configured to receive the fuel injection include a third mixing passage arranged angled to the central axis and located between the first and second mixing passages. A fourth example of the system, optionally including the first through third examples, further includes where the first, second, and third mixing passages are integrated into a cylindrical duct, where a portion of the duct is coupled to the fuel injector in the cylinder head and where a remaining portion of the duct comprising the mixing passages is below the cylinder head.

An embodiment of a method comprises decreasing a combustion chamber temperature in response to an amount of light sensed in a passage fluidly coupling a fuel injector to the combustion chamber. A first example of the method further includes where the amount of light to a threshold light, the threshold light being based on light released in the passage when soot is produced above a desired amount. A second example of the method, optionally including the first example, further includes where decreasing the combustion chamber temperature includes flowing EGR to the combustion chamber, decreasing manifold pressure, decreasing an intake manifold temperature, and injecting water into the combustion chamber. A third example of the method, optionally including the first and/or second examples, further includes where sensing the amount of light via a photodiode located in the passage. A fourth example of the method, optionally including one or more of the first through third examples, further includes where mixing fuel with combustion chamber gases in the passage. A fifth example of the method, optionally including one or more of the first through fourth examples, further includes where the passage is located below a cylinder head, the passage is configured to direct a fuel injection into the combustion chamber.

An embodiment of a system comprising a fuel injector located in a cylinder head, a passage located below the cylinder head in a combustion chamber, the passage aligned with a fuel injector orifice of a nozzle of the fuel injector, and a controller with computer-readable instructions that when implemented allow the controller to decrease a cylinder temperature in response to an amount of light measured by a light sensor in the passage being greater than a threshold amount of light. A first example of the system further includes where the passage is located in a duct, the duct being coupled to the cylinder head along a central axis of the fuel injector. A second example of the system, optionally including the first example, further includes where the passage is a single passage of a plurality of mixing passages located on the duct, and where the mixing passages are fluidly coupled to one another, and where first and second passages of the mixing passages are misaligned with the fuel injector orifice and are angled to a direction of a fuel injection, and where third passages are aligned with each fuel injector orifice of the nozzle. A third example of the system, optionally including the first and/or second examples, further includes where the first passages extend in a radially outward direction perpendicular to the central axis of the fuel injector, the second passage extends in a vertical direction along the central axis of the fuel injector, and the third passages extend in a direction oblique to the central axis of the fuel injector. A fourth example of the system, optionally including one or more of the first through third examples, further includes where the third passages are located between the first and second passages. A fifth example of the system, optionally including one or more of the first through fourth examples, further includes where the passage is integrated into a tip of the nozzle. A sixth example of the system, optionally including one or more of the first through fifth examples, further includes where the passage is one or a plurality of passages including a first passage and a third passage aligned along a central axis of the fuel injector, and where a plurality of second passages are fluidly coupled to the third passage. A seventh example of the system, optionally including one or more of the first through sixth examples, further includes where the first and third passages direct a fuel injection toward the combustion chamber, and where the second passages direct combustion chamber gases to the third passage. An eighth example of the system, optionally including one or more of the first through seventh examples, further includes where the controller decreases the cylinder temperature by one or more of increasing an EGR flow rate, decreasing an intake manifold pressure and temperature, and increasing an in-cylinder water injection.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A system comprising:
   a fuel injector comprising a nozzle tip submerged into a combustion chamber below an end wall of a cylinder head, the nozzle tip comprising one or more fuel injection orifices configured to inject at an angle relative to a central axis of the fuel injector; and
   one or more mixing passages configured to receive a fuel injection or combustion chamber gases, where the one or more mixing passages configured to receive the fuel injection are oblique to the central axis and are aligned with the fuel injection orifices, and where there are more mixing passages configured to receive combustion chamber gases than mixing passages configured to receive the fuel injection.

2. The system of claim 1, wherein the one or more mixing passages are integrated into the nozzle tip and are configured to receive combustion chamber gases and include upper passages and lower passages angled relative to a central axis, wherein the upper passages form an angle between 60-90 degrees with the central axis and the lower passages form an angle between 0-30 degrees with the central axis, and where the lower passages are further away from the cylinder head than the upper passages.

3. The system of claim 2, wherein each of the one or more mixing passages configured to receive the fuel injection are located between the upper and lower passages, and where the one or more passages configured to receive the fuel injection increase in diameter at an intersection where the upper and lower passages are fluidly coupled to the one or more passages configured to receive the fuel injection, and where one or more of the mixing passages comprises one or more of a venturi passage and a louver.

4. The system of claim 1, wherein the one or more mixing passages configured to receive combustion chamber gases include a first mixing passage arranged adjacent to the cylinder head and a second mixing passage arranged distal to the cylinder head, where the first mixing passage forms an angle relative to the central axis between 60 to 90 degrees and the second passage forms an angle relative to the central axis between 0 and 30 degrees, and where the one or more mixing passages configured to receive the fuel injection include a third mixing passage arranged angled to the central axis and located between the first and second mixing passages.

5. The system of claim 4, wherein the first, second, and third mixing passages are integrated into a cylindrical duct, where a portion of the duct is coupled to the fuel injector in the cylinder head and where a remaining portion of the duct comprising the mixing passages is below the cylinder head.

6. A method comprising:
   decreasing a combustion chamber temperature in response to an amount of light sensed in a passage fluidly coupling a fuel injector to the combustion chamber.

7. The method of claim 6, further comprising the amount of light to a threshold light, the threshold light being based on light released in the passage when soot is produced above a desired amount.

8. The method of claim 6, wherein decreasing the combustion chamber temperature includes flowing EGR to the combustion chamber, decreasing manifold pressure, decreasing an intake manifold temperature, and injecting water into the combustion chamber.

9. The method of claim 6, further comprising sensing the amount of light via a photodiode located in the passage.

10. The method of claim 6, further comprising mixing fuel with combustion chamber gases in the passage.

11. The method of claim 6, wherein the passage is located below a cylinder head, the passage is configured to direct a fuel injection into the combustion chamber.

12. A system, comprising:
a fuel injector located in a cylinder head;
a passage located below the cylinder head in a combustion chamber, the passage aligned with a fuel injector orifice of a nozzle of the fuel injector; and
a controller with computer-readable instructions that when implemented allow the controller to:
decrease a cylinder temperature in response to an amount of light measured by a light sensor in the passage being greater than a threshold amount of light.

13. The system of claim 12, wherein the passage is located in a duct, the duct being coupled to the cylinder head along a central axis of the fuel injector.

14. The system of claim 13, wherein the passage is a plurality of mixing passages located on the duct, and where the mixing passages are fluidly coupled to one another, and where first and second passages of the mixing passages are misaligned with the fuel injector orifice and are perpendicular and parallel to a direction of a fuel injection, respectively, and where third passages are aligned with each fuel injector orifice of the nozzle.

15. The system of claim 14, wherein the first passages extend in a radially outward direction perpendicular to the central axis of the fuel injector, the second passage extends in a vertical direction along the central axis of the fuel injector, and the third passages extend in a direction oblique to the central axis of the fuel injector.

16. The system of claim 14, wherein the third passages are located between the first and second passages, and where each of the first and second passages are fluidly coupled to each of the third passages located therebetween.

17. The system of claim 12, wherein the passage is integrated into a tip of the nozzle.

18. The system of claim 17, wherein the passage divides into a plurality of passages including a first passage and a third passage aligned along a central axis of the fuel injector, and where a plurality of second passages are fluidly coupled to the third passage.

19. The system of claim 18, wherein the first and third passages direct a fuel injection toward the combustion chamber, the third passage comprising a larger radius than the first passage, and where the second passages direct combustion chamber gases to the third passage, and where the second passages extend from a trifurcation of the first passage to a lowest portion of the nozzle tip adjacent the combustion chamber.

20. The system of claim 12, wherein the controller decreases the cylinder temperature by one or more of increasing an EGR flow rate, decreasing an intake manifold pressure and temperature, and increasing an in-cylinder water injection.

* * * * *